US012727891B2

(12) United States Patent
Rodriques et al.

(10) Patent No.: US 12,727,891 B2
(45) Date of Patent: Sep. 8, 2026

(54) AUTOMATED DRILLING DEVICE AND METHOD

(71) Applicant: Clee Medical SA, Geneva (CH)

(72) Inventors: Samuel G. Rodriques, Wilmington, DE (US); David J. Segar, Wilmington, DE (US); Jonathan Betts-LaCroix, Wilmington, DE (US); Jérôme Gandar, Geneva (CH); Matthew Lapinski, Geneva (CH)

(73) Assignee: Clee Medical SA, Geneva (CH)

( * ) Notice: Subject to any disclaimer, the term of this patent is extended or adjusted under 35 U.S.C. 154(b) by 235 days.

(21) Appl. No.: 18/554,967

(22) PCT Filed: Apr. 20, 2022

(86) PCT No.: PCT/US2022/071815
§ 371 (c)(1),
(2) Date: Oct. 11, 2023

(87) PCT Pub. No.: WO2022/226506
PCT Pub. Date: Oct. 27, 2022

(65) Prior Publication Data

US 2024/0197339 A1 Jun. 20, 2024

Related U.S. Application Data

(60) Provisional application No. 63/177,268, filed on Apr. 20, 2021.

(51) Int. Cl.
*A61B 17/16* (2006.01)

(52) U.S. Cl.
CPC ...... *A61B 17/1626* (2013.01); *A61B 17/1615* (2013.01); *A61B 17/1695* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS

| | | | | |
|---|---|---|---|---|
| 5,460,182 A * | 10/1995 | Goodman | ............ | A61B 5/0084 600/478 |
| 6,109,270 A | 8/2000 | Mah et al. | | |

(Continued)

FOREIGN PATENT DOCUMENTS

| | | |
|---|---|---|
| CN | 101530341 A | 9/2009 |
| CN | 109195544 A | 1/2019 |

(Continued)

OTHER PUBLICATIONS

Communication Pursuant to Article 94(3) EPC for EP 22723939.9, dated Mar. 25, 2025.

(Continued)

*Primary Examiner* — Eric S Gibson
(74) *Attorney, Agent, or Firm* — Hamilton, Brook, Smith & Reynolds, P.C.

(57) ABSTRACT

A surgical device for automated drilling includes a drill comprising a drill bit configured to bore through bone and a detector comprising a tissue detection sensor. The drill and detector are independently actuable for insertion and removal of the drill bit and the tissue detection sensor in a bore generated by the drill bit. A surgical system can include the surgical device and a controller configured to actuate the drill to bore through bone, actuate the drill to retract the drill bit from the bore, actuate the detector to insert the tissue detection sensor into the bore, and determine a tissue characteristic at a distal location of the bore based on a sensed signal from the tissue detection sensor.

9 Claims, 12 Drawing Sheets

(58) Field of Classification Search

CPC ............ A61B 17/1622; A61B 17/1624; A61B 17/1626; A61B 17/1628; A61B 17/1655; A61B 17/1657; A61B 17/1695; A61B 34/32; A61B 2090/065; A61B 2090/066

See application file for complete search history.

(56) References Cited

U.S. PATENT DOCUMENTS

| | | | | |
|---|---|---|---|---|
| 6,336,931 | B1 * | 1/2002 | Hsu | A61B 17/1626 606/130 |
| 9,463,031 | B2 * | 10/2016 | Radermacher | A61B 17/1695 |
| 2002/0177843 | A1 | 11/2002 | Anderson et al. | |
| 2013/0274750 | A1 * | 10/2013 | Schoutens | A61B 17/1615 606/80 |
| 2016/0000448 | A1 * | 1/2016 | Houssiere | A61B 17/1628 606/130 |
| 2016/0296242 | A1 * | 10/2016 | Pak | A61B 17/1695 |
| 2016/0302930 | A1 * | 10/2016 | Axelrod | A61F 2/30756 |
| 2018/0250020 | A1 * | 9/2018 | Carusillo | A61B 90/06 |
| 2019/0029697 | A1 * | 1/2019 | Anderson | A61B 17/1622 |
| 2020/0008889 | A1 * | 1/2020 | Ho | A61B 17/34 |
| 2020/0297358 | A1 | 9/2020 | Cameron et al. | |
| 2020/0297382 | A1 * | 9/2020 | Coppedge | A61B 17/3472 |
| 2021/0113239 | A1 * | 4/2021 | Donovan | A61B 17/3421 |
| 2022/0378526 | A1 * | 12/2022 | Balicki | A61B 34/32 |
| 2024/0197339 | A1 * | 6/2024 | Rodriques | A61B 90/03 |

FOREIGN PATENT DOCUMENTS

| | | | | | |
|---|---|---|---|---|---|
| DE | 102007050017 | B4 | * | 7/2021 | A61B 17/1695 |
| KR | 10-2019-0074069 | A | | 6/2019 | |
| WO | WO-9827887 | A1 | * | 7/1998 | B25J 9/1692 |
| WO | WO-9833451 | A1 | * | 8/1998 | A61B 90/10 |
| WO | 2013098555 | A1 | | 7/2013 | |
| WO | 2016199152 | A1 | | 12/2016 | |
| WO | WO-2018136622 | A1 | * | 7/2018 | B22F 10/36 |
| WO | WO-2021050767 | A1 | * | 3/2021 | A61B 18/082 |
| WO | WO-2021089550 | A1 | * | 5/2021 | B25J 9/1666 |
| WO | WO-2022226506 | A1 | * | 10/2022 | A61B 17/1626 |

OTHER PUBLICATIONS

International Search Report and Written Opinion for International Appl. No. PCT/US2022/071815, entitled "Automated Drilling Device and Method," consisting of 13 pages. Dated: Jul. 28, 2022.

CARS 2019—Computer Assisted Radiology and Surgery Proceedings of the 33rd International Congress and Exhibition, Rennes, France, Jun. 18-21, 2019 ED—Barratt D; Jannin P; Fichtinger G; Cotin S, May 18, 2019 (May 18, 2019), vol. 14, No. 1, p. 1-194.

* cited by examiner

Move to new location 716

Terminate drilling 714

Yes

Drill to intial depth 702

Retract drill 704

Insert detector 706

Tissue characteristic determination 710

Blood vessels detected? 712

No

Drill additional depth 724

Insert drill 722

Retract detector 720

Desired depth reached? 718

Insert diagnostic / therapeutic device 726

AUTOMATED DRILLING DEVICE AND METHOD

RELATED APPLICATION(S)

This application is the U.S. National Stage of International Application No. PCT/US2022/071815, filed Apr. 20, 2022, which designates the U.S., published in English, and claims the benefit of U.S. Provisional Application No. 63/177,268, filed on Apr. 20, 2021. The entire teachings of the above applications are incorporated herein by reference.

BACKGROUND

Many medical procedures involve the delivery of drugs to intracranial or intraventricular spaces, often because chemotherapeutics or biologics do not effectively cross the blood-brain barrier. Current procedures for accessing the intracranial spaces are highly invasive.

For example, adult leukemia patients often require delivery of intracranial chemotherapeutics via an implanted medical device, such as an Ommaya reservoir. For Ommaya reservoir implantations, a neurosurgeon makes a 5-10 cm incision in the scalp, drills a 1-1.5 cm burr hole through the skull, and passes a 3.5 mm catheter through the brain and into the ventricles. This catheter is left in place, connected to a reservoir lying on the surface of the skull, and the scalp is closed in layers over the site. This surgical procedure induces significant patient distress, and wound breakdown and infection associated with implantation are common and can be devastating. Furthermore, these device implantations often prevent immediate initiation of chemotherapy, as the surgical wounds must heal. Alternatives, such as intrathecal delivery, are also limiting from a quality of life perspective.

There exists a need for improved devices and methods for providing access to intracranial and intraventricular spaces.

SUMMARY

Devices and methods for automated microsurgery are provided, with such devices and methods capable of reducing complications and distress associated with insertion and delivery of drugs into anatomical spaces located in or behind bone, such as the brain and spine.

A surgical device for automated drilling includes a drill comprising a drill bit configured to bore through bone and a detector comprising, or configured to releasably receive, a tissue detection sensor. The drill and detector are independently actuable for insertion and removal of the drill bit and the tissue detection sensor, respectively, in a bore generated by the drill bit.

The drill and detector can be disposed on a stage element and are configured for selective attachment to a motorized frame. The tissue detection sensor can be an interferometric device or sensor, for example, an optical probe for optical coherence tomography (OCT). The tissue sensor can be, in other examples, a backscatter probe, a temperature detector, pressure sensor, or infrared detector. Optionally, the detector can include two or more types of tissue detection sensors. The stage element can be indexable with motors, for example, manual manipulation.

The device can further include a backpressure sensor configured to detect a pressure exerted on the drill bit during drilling, a torque sensor configured to detect a torque applied by an actuator of the drill, or both a backpressure sensor and a torque sensor. The backpressure and torque sensors can, each independently or together, provide for detection of the drill moving from more to less dense tissue (e.g., a break-through from bone).

The drill bit can have a diameter of less than about 2 mm, or of less than about 1 mm. A diameter of the drill bit can be in range of about 200 μm to about 2 mm, or in range of about 200 μm to about 1 mm. The drill bit can be configured for drilling to a depth of at least about 15 mm, or at least about 7 mm. The drill bit can be made of titanium, stainless steel, or any other sufficiently strong and stiff material to bore through bone while retaining structural integrity, resisting deflection, and/or providing head dissipation so as to burn tissue during drilling.

The device can further include a chassis or other receptacle (e.g., a tool cell) to removably or fixedly receive additional tissue detection sensors, therapeutic devices, and diagnostic devices for use with the device. The additional chassis can permit independent actuation of at least a component of the therapeutic or diagnostic device for insertion and removal in the bore generated by the drill bit. Examples of suitable diagnostic and therapeutic devices include a cannula (e.g., a needle, catheter), an electrocautery element, an electrical probe, a pressure sensor (e.g., an intracranial pressure sensor), a biopsy device, a surgical device (e.g., blade, needle, trocar, aspirator, etc.), and an ablation device (e.g., laser ablation device). The detector, or a portion thereof (e.g., a chassis of the detector, alternatively referred to as a detector cell) can optionally be configured to receive other diagnostic or therapeutic devices. For example, the tissue detection sensor, such as an optical probe, can be removeable from the detector cell and an additional tool (e.g., a diagnostic and/or therapeutic device) can be received in the detector cell for use with the device. Alternatively, or in addition, additional tool cells can be included on a stage. For example, a tool cell, in addition to a detector cell and a drill cell, can be included at the stage element and independently actuable for delivery of a therapy or a diagnostic device.

A surgical system for automated drilling can include a surgical device and a controller configured to operate the device. The controller can be configured to actuate the drill to bore through bone, actuate the drill to retract the drill bit from the bore, actuate the detector to insert the tissue detection sensor into the bore, and determine a tissue characteristic at a distal location of the bore based on a sensed signal from the tissue detection sensor. Optionally, the controller can be configured to advance a surgical, diagnostic or therapeutic device to a targeted site.

The controller can be a processor and any associated electronics, which can be disposed external to the surgical device. The determination of the tissue characteristic can include any or all of the following, in any combination: determination of a change in anatomy at or near the distal location, determination of a presence of a blood vessel at or near the distal location, determination of a thickness of a tissue layer at the distal location, and determination of a density of a tissue layer at the distal location.

The controller can be further configured to detect a penetration of the drill bit from a more rigid tissue to a less rigid tissue based on a pressure as detected by the backpressure sensor, a torque as detected by the torque sensor, or a combination thereof. The controller can halt drilling based on the detected penetration. Alternatively, or in addition, the controller can be configured to actuate the drill to drill to a defined depth prior to actuation of the tissue detection sensor.

The controller can be configured to actuate the stage element for selective attachment of the drill (e.g., drill cell) and the detector (e.g., detector cell) to the motorized frame, and, optionally, for a tool (e.g., a tool cell for a diagnostic or therapeutic device, including, for example, a surgical tool). The controller can be further configured to actuate translation of the motorized frame to dispose one of the drill, the detector, and the therapeutic/diagnostic device at the bore. Linear movement (e.g., one-dimensional movement and/or multi-dimensional movement, including, for example, movement in plane and/or out of plane, such as movement along a wave-shaped path), rotational movement, or a combination thereof can be actuated by the controller for moving the detector and/or a therapeutic or diagnostic device through the bore.

An automated drilling method includes, with a drill comprising a drill bit, drilling a bore through bone and removing the drill bit from the bore. The method further includes, with a detector comprising a tissue detection sensor, inserting the tissue detection sensor into the bore and detecting a tissue characteristic at a distal location of the bore based on a sensed signal from the tissue detection sensor. The drill and the detector are independently actuable for insertion and removal of the drill bit and the tissue detection sensor in the bore generated by the drill bit.

The method can further include translating a stage element upon which the drill and the detector are disposed for selective attachment of one of the drill bit and the tissue detector sensor to a motorized frame to dispose the one of the drill bit and the tissue detector at the bore.

Detecting the tissue characteristic can include determining at least one of a presence of a blood vessel at or near the distal location, a change in anatomy at or near the distal location, a thickness of a tissue layer at the distal location, and a density of a tissue layer at the distal location. The determination can be based on any or all of the following, in any combination: interferometry (e.g., optical coherence tomography (OCT)), backscatter, temperature, pressure, and infrared measurements.

The method can further include detecting at least one of a change in pressure exerted on the drill bit during drilling and a change in torque applied by an actuator of the drill. A penetration of the drill bit from a more rigid tissue to a less rigid tissue or from a less rigid tissue to a more rigid tissue, can be detected based on the detected change in pressure, the detected change in torque, or a combination thereof. Based on the detected change, drilling of the bore can be halted.

The method can further include actuating the detector to remove the tissue detection sensor from the bore and actuating a therapeutic or diagnostic device for the insertion of at least a component of the therapeutic or diagnostic device into the bore. The therapeutic device can be, for example, a cannula, and a drug can be delivered via the cannula to a location in or distal to the bore. In another example, the therapeutic device can be an electrocautery system, or a component thereof, and tissue at a location in or distal to the bore can be cauterized. The therapeutic device can be a laser ablation device, and the method can include ablating a tissue at a location in or distal to the bore. An electrical probe can be inserted into the bore, which can function as a therapeutic and/or diagnostic device. For example, the method can include at least one of electrical recording and electrical stimulation (e.g., deep brain stimulation) at a location in or distal to the bore. The electrical recording can be, e.g., of brain activity in an epileptic patient.

In another example, the diagnostic device can be a biopsy device, and the method can include obtaining a tissue sample from a location in or distal to the bore. The diagnostic device can be a cannula, and the method can include extracting a tissue or fluid from a location in or distal to the bore. A pressure sensor can be inserted, and the method can include measuring a pressure from a location in or distal to the bore.

A method of operating a surgical device includes actuating the drill to bore through bone, actuating the drill to retract the drill bit from the bore, and actuating the detector to insert the tissue detection sensor into the bore. The method further includes determining a tissue type or a tissue characteristic at a distal location of the bore based on a sensed signal from the tissue detection sensor.

The bone can be, for example, skull. Alternatively, the bone can be a vertebra. The surgical devices and systems provided herein are generally described with respect to applications at the skull. However, the surgical devices and systems provided can be used for operations at other anatomy. For example, it may be desirable to bore through a vertebra to access a portion of the spine, or to bore through other bones to access, for example, marrow (e.g., the iliac crest for a bone marrow biopsy) or a potential tumor for biopsy, or to bore through bone to facilitate placement of internal fixation devices.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1A:
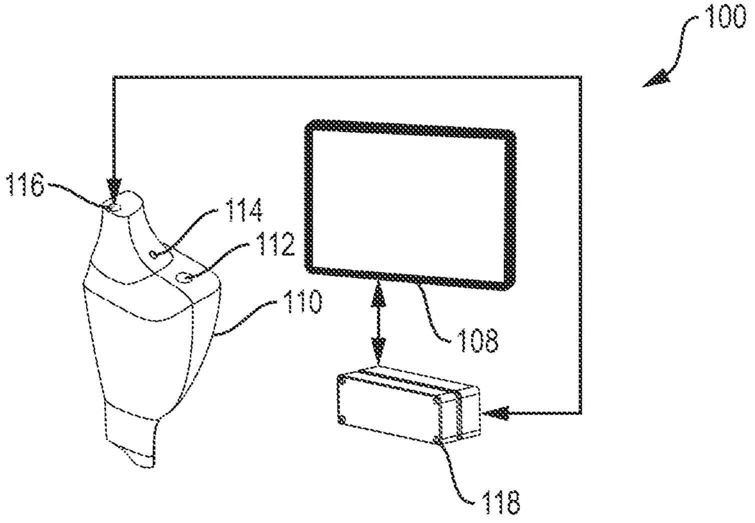
FIG. 1A is a schematic of an example surgical system.

The surgical systems, devices and methods described can provide for precise, efficient, and automated drilling of bone in conjunction with automated detection of anatomical tissues (e.g., bone, blood vessels, parenchyma, tumors, ventricles, and cerebellum), which can be used to inform both drilling and subsequent delivery of other devices to the intracranial space. The surgical devices and methods described can provide a solution to the shortcomings of manual surgery for accessing the intracranial space and can provide for several advantages over existing neurosurgical systems.

While several devices have been developed to aid in stereotactic neurosurgical targeting, such as the Rosa One® brain platform (Zimmer Biomet) and the Neuromate® robotic system (Renishaw), the scale of drilling performed by such systems is above several millimeters in diameter and such systems are not fully automated. Systems such as the Craniobot® (LABmaker) provide for micrometer scale milling operations for removing a sub-millimeter thick mouse skull, but are inadequate for operations on, for example, human skulls. Robotic systems have been developed to guide surgical procedures using computer vision, but such systems rely on cameras to guide the robotic surgery system in a macroscopic surgical field and, thus, can be of inadequate precision for brain applications. OCT has been integrated with biopsy needles, however, such devices are not suitable for applications involving bone.

The surgical devices and methods provided can automatically detect blood vessels and tissue boundaries to guide drilling on a microsurgical scale. As used herein, the terms "microsurgery" and "microsurgical" refer to surgeries occurring at a scale of less than about 2 mm. For example, the systems and methods described can provide for the drilling, through bone, of holes having a diameter ranging about 200 μm to about 2000 μm. The microsurgical devices described can provide for greatly improved healing and bone regrowth and can significantly reduce patient distress as compared with manual drilling procedures and with drilling produced by existing robotic surgical devices.

As it would be practicably impossible for a surgeon to manually control drill bits of such small diameters, the devices and methods described involve automated drilling with integrated safety systems, such as integrated optical and/or mechanical measurement systems for detecting blood vessels and preventing injury to underlying brain tissue. The automated microsurgical systems and methods described can enable a smaller hole to be produced than that which could be practicably drilled by hand, with such smaller holes resulting in reduced patient recovery time, a lower risk of post-surgical infection, and more complete patient tissue healing.

The systems and methods described can also provide for the detection of various tissue types, which can decrease the risk of hemorrhage (e.g., during both drilling and subsequent delivery of a diagnostic or therapeutic device). The system can inform an operator if there is a blood vessel present at or near a distal end of a detection probe of the device. The probe can be sized to fit within the drilled hole. For example, a distal end of the probe can be of a size between about 180 μm and 1.99 mm. The detection of tissues can also increase confidence with respect to a determination of a location of the distal end of the probe, as the user can be informed if, for example, the distal end enters different tissue type (e.g., a tumor).

A description of example embodiments follows.

Figure 1B:
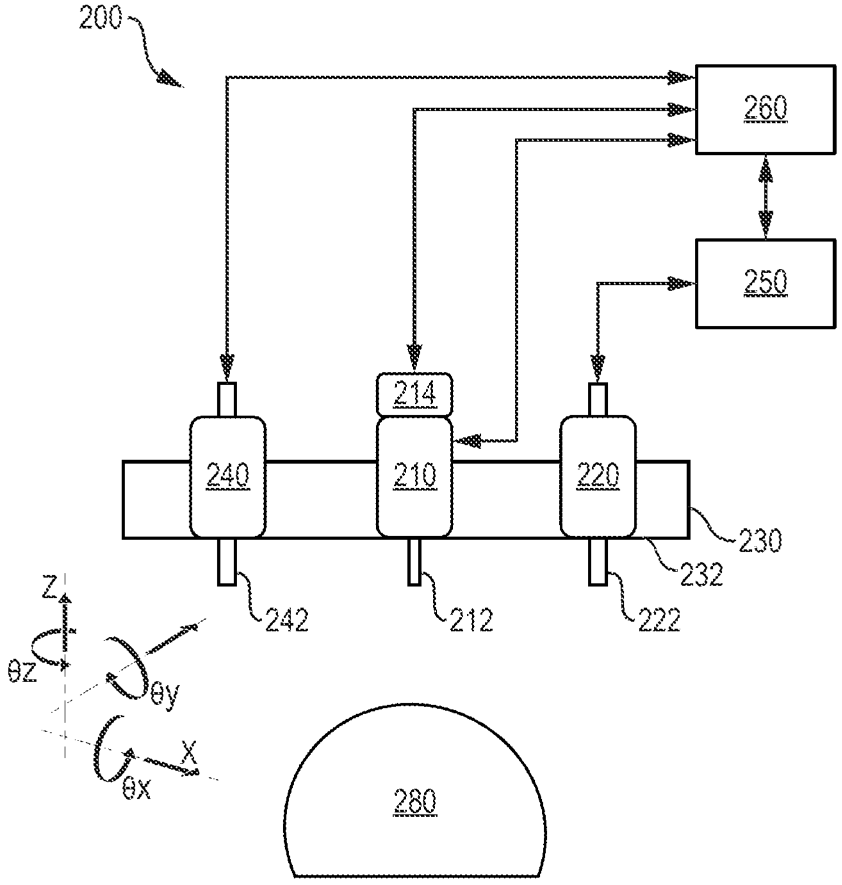
FIG. 1B is a schematic of components of the example surgical system of FIG. 1A.

An example surgical system 100 is shown in FIG. 1A, which includes a surgical device 110, electronics 118, and a user input/output controller 108. The term "controller" as used with respect to FIG. 1 refers to a user input/output device as opposed to merely a processor. The surgical device 110, electronics 118 and controller 108 can be communicatively coupled through wired and/or wireless connections. The surgical device 110 can be in contact with a patient and can perform actions related to drilling and tissue characteristic detection, and, optionally, actions relating to the delivery of diagnostic or therapeutic devices, including other surgical devices. The electronics 118 associated with operation of the device 110 can be internal or external to the device 110. A user or operator of the system can interface with the controller 108 to direct actions of the surgical device 110 and interpret data obtained by or through use of the device 110.

The surgical device 110 can include ports 112, 114, 116 to provide for access of various components. For example, the port 116 can provide for wired communication of various actuators of the device to the external electronics 118. The port 114 can provide access for loading tools or tool components into or through the device (e.g., optical cables of an OCT detector, catheters, etc.). The port 112 can provide access for power cables of motorized components of the device. Additional or fewer ports can be included.

Figure 2:
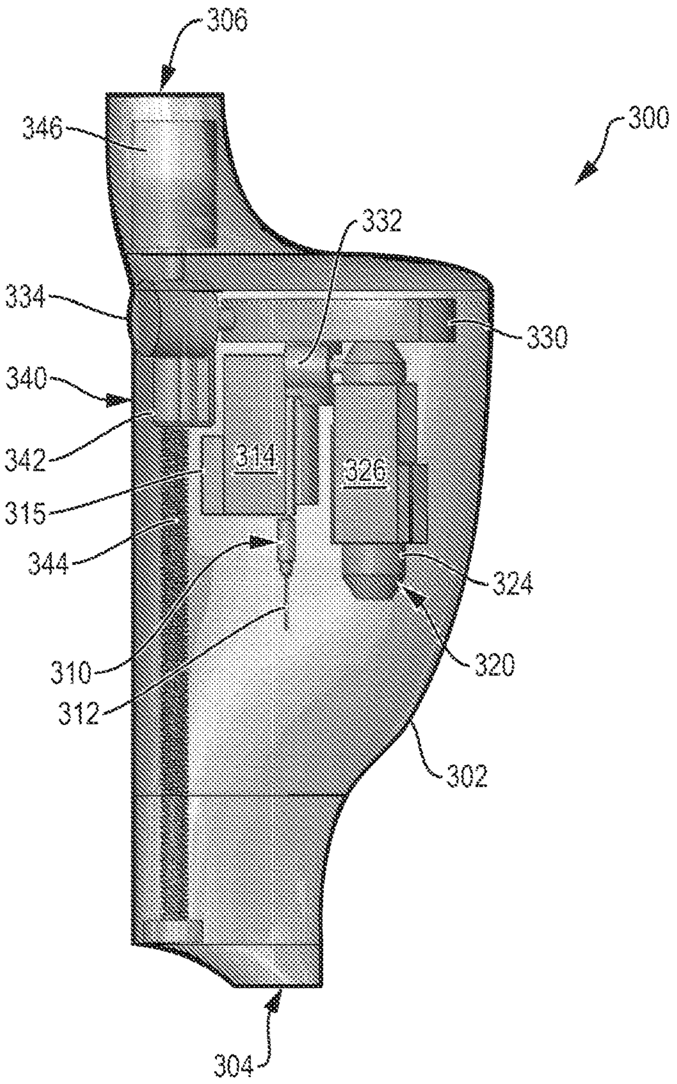
FIG. 2 illustrates an example surgical device including a drill and a detector.

A schematic of components of a surgical device for automated drilling is shown in FIG. 2. The surgical device 200 includes a drill 210 having a drill bit 212 configured to bore through bone and a detector 220 having a tissue detection sensor 222. For example, the detector can be an OCT detector, and the sensor 222 can be an optical probe.

Optionally, a tool delivery element 240 can be included in the device to provide for connection with a therapeutic or diagnostic device. For example, the tool delivery element 240 can be configured to removably receive a therapeutic or diagnostic device 242, such as a cannula or an electrical probe. The therapeutic or diagnostic device can be, for example, an additional surgical device (other than the drill bit). Some devices, such as cannulas, can be both a therapeutic device and a diagnostic device. For example, a cannula can be provided to dispense a therapy (e.g., a drug), to dispense a diagnostic agent (e.g., contrast agents for imaging), or to perform a diagnostic procedure (e.g., to aspirate biological materials for sampling or biopsy, such as for sampling of cerebral spinal fluid (CSF)).

As illustrated, the drill 210, detector 220, and optional tool delivery element 240 are disposed on a stage element 230. The stage element 230 can itself be moveable to dispose any one of the drill 210, detector 220, and tool delivery element 240 at a subject 280. For example, the stage element can be couplable to a motorized frame (e.g., FIG. 13). Alternatively, or in addition, the stage element 230 can be included within a housing of the device (e.g., FIG. 2) and can be configured to provide for selective coupling of the drill 210, detector 220, and tool delivery element 240 to a motorized frame at least partially disposed within the housing.

Figure 12:
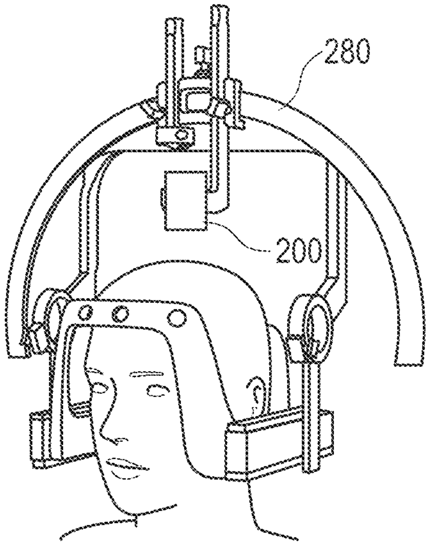
FIG. 12 illustrates an example environment in which a surgical system can be deployed, including an example neurosurgical frame.

The device 200 can be coupled to an external stereotactic device 280, such as a frame or robot, as shown in FIG. 12. Examples of suitable stereotactic devices 280 include the Leksell® systems (Elekta), the CRW® instruments (Integra), the STarFix™ platforms (FHC), the Rosa One® platforms (Zimmer Biomet), and the Neuromate® robotic systems (Renishaw).

Among position control provided by motorized elements that are directly and/or indirectly attached to the stage element 230, each of the drill 210, detector 220, and optional tool delivery element 240 can be translated along three linear axes (X,Y,Z) and/or along at least two of three angular axes (θx,θy,θz) to position the device components at the subject 280.

The detector 220 can be or include, for example, an interferometric device, such as an OCT system or a component thereof, with a probe 222 of the system operably coupled to an OCT base station 250 at which optical signals can be collected and processed. An example of a suitable OCT system is the Telesto® OCT system (ThorLabs). The system further includes a processor 260, operably connected to each of the drill 210, detector 220, and optional tool delivery element 240, and, optionally, to the OCT base station 250.

The drill 210 can optionally include one or more sensor(s) 214. The sensor 214 can be a backpressure sensor configured to detect a pressure exerted on the drill bit during drilling or a torque sensor configured to detect a torque applied by an actuator of the drill. Optionally, both a backpressure sensor and a torque sensor can be included in the device.

An example surgical device 300 is shown in FIG. 2. The device includes a housing 302 within which a drill 310 and a detector 320 are disposed. The drill 310 includes a drill bit 312. The drill bit 312 can be removably couplable to the drill 310 such that varying size drill bits can be used by an operator of the device. The detector 320 can be configured to receive or house a tissue detection sensor, such as an OCT probe. For example, an optical cable can be threaded through a detector guide 324, as further shown and described in FIGS. 6 and 7A-B. Alternatively, an optical detector can be integrated within the detector guide 342, as further shown in FIGS. 15A-B. The drill element 310 and detector element 320 element are alternatively referred to herein as a drill cell and a detector cell.

The drill cell and the detector cell can be independently actuable for insertion and removal of, respectively, the drill bit and the tissue detection sensor in a bore generated by the drill bit. For example, as illustrated in FIG. 2, the drill cell 310 and detector cell 320 are disposed on a stage element 330. The cells can be releasably coupled to the stage element via a rotational coupling 334 to enable switching between the drill 310 and the detector 320 at a location close to a motorized frame 340, from which location the cells can engage with a component of the frame.

Figure 3:
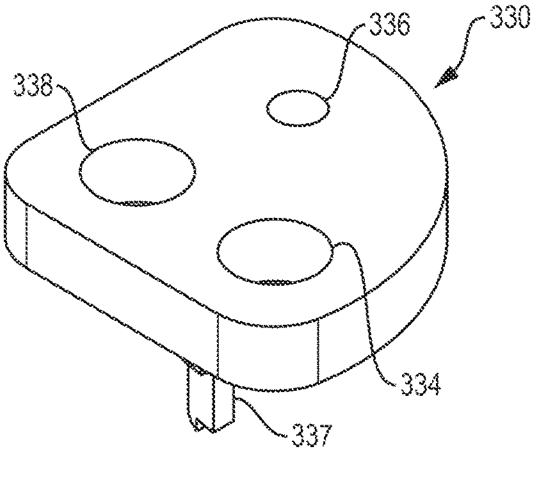
FIG. 3 illustrates a stage element of the example surgical device of FIG. 2.

An example configuration of the stage element 330 is shown in FIG. 3. The stage element 330 includes ports 334, 338 to provide through-access to each of the cells, such as may be required for wires, cables, etc. connecting to each cell. While the stage element is shown in FIGS. 2 and 3 as including only two cells, additional cells can be included in the device. For example, additional port(s) 336 can be included to provide for connective access for cells for additional tools. As illustrated, the stage is configured to rotate about an arc to provide for switching of an active cell; however, other configurations are possible. For example, the stage can be configured to rotate about a single point, as a cam, or to move linearly. Movement of the stage can be controlled by an actuator, such as a motor or pneumatic device, or can be manually-controlled. The stage can include a connecting element 337 for engagement with a cell.

Returning to FIG. 2, the motorized frame 340 can include a coupling element 342, which can translate along a lead screw 344, and a motor 346. The positioning of one of the drill cell 310 and the detector cell 320 closest to the motorized frame can enable translation of the selected cell toward a surgical port 304 located at a base of the device. Each of the cells can include a complementary coupling element (i.e., a drill coupling element 314 and a detector coupling element 326) for engaging with the coupling element 342 of the motorized frame.

Figure 4:
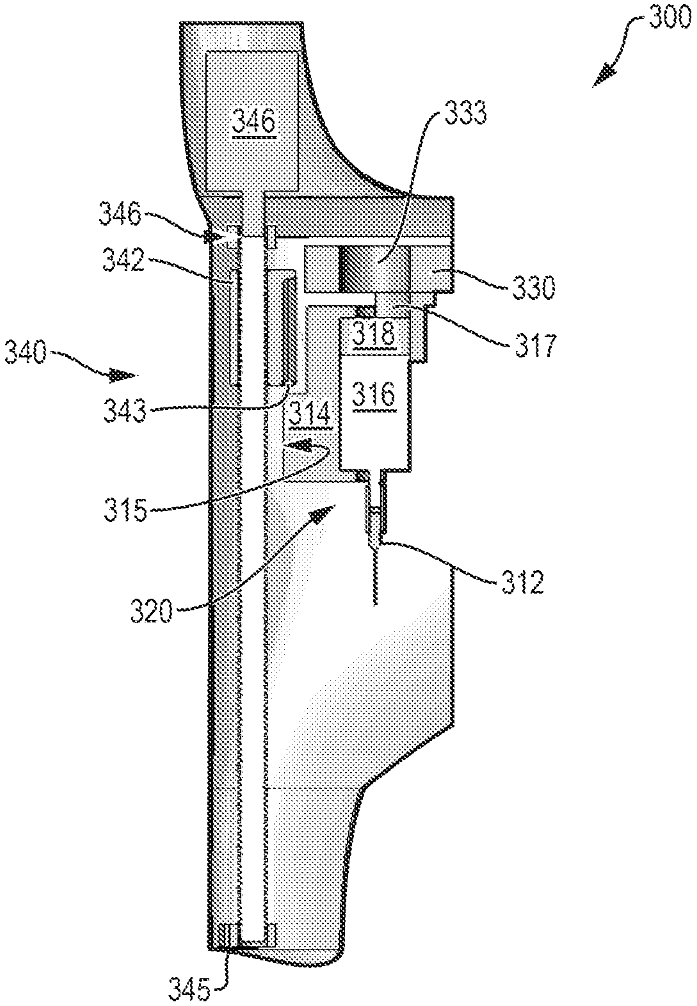
FIG. 4 is a cross-section view of the surgical device shown in FIG. 2, illustrating an example selective attachment mechanism.

As further shown in FIG. 4, with the drill cell 320 shown as an example, each cell can be releasably couplable from both the stage element 330 and the motorized frame 340. For example, the drill cell 320 can include a drill-stage coupling element 317 and a drill-frame coupling element 314. The stage 330 can include a coupling element 333 that is complementary to the drill-stage coupling element 317. Similarly, the motorized frame coupling element 342 can be complementary to coupling elements 314, 326 for engaging the drill cell and the detector cell. The coupling elements can include, for example, magnets, clips, mechanical couplings, interference attachments, or the like. As illustrated, and for example, the coupling elements 317 and 333 are magnetically engaged, and the coupling element 342 includes a track 343 configured to engage with a projection 315 of the coupling element 314. The coupling element 342, as illustrated, is a nut configured to translate along the lead screw 344. An actuator 346 can drive the lead screw to control proximal and distal translation of the coupling element 342. The lead screw 344 can be retained by an end support 345 at a proximal end of the device, and by an end support 346 at a distal end of the device. The actuator 346 can be a motor or a pneumatic device, for example. Also illustrated in FIG. 4 are an actuator 316 and a sensor 318 associated with the drill.

Figure 5:
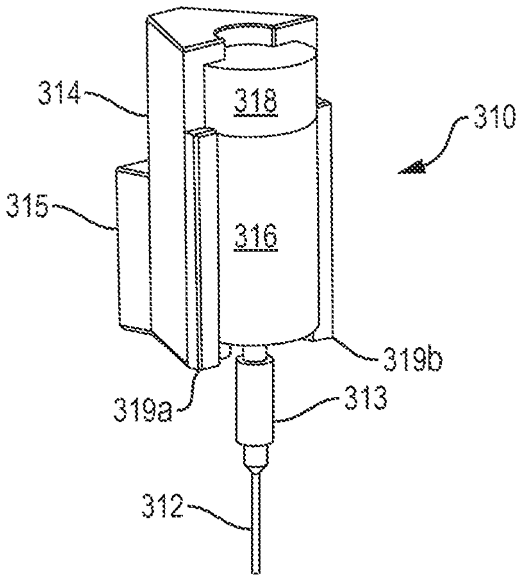
FIG. 5 illustrates an example drill element, alternatively referred to as a drill cell.

The drill cell 320 is further shown in FIG. 5. As illustrated the drill components (i.e., drill bit 312, actuator 316, and sensor 318) can be retained within the coupling element 314 by retaining elements 319*a*, 319*b*. The drill components can be releasably retained within the drill cell. A drill bit coupler 313 can provide for secure coupling of the drill bit 312 to the actuator 316. The sensor 318 can be, for example, a backpressure sensor configured to detect a pressure exerted on the drill bit during drilling or a torque sensor configured to detect a torque applied by an actuator of the drill. Optionally, both a backpressure sensor and a torque sensor can be included in the drill cell. As illustrated, the sensor 318 abuts the actuator 316; however, the sensor can alternatively be offset from the actuator.

Figure 6:
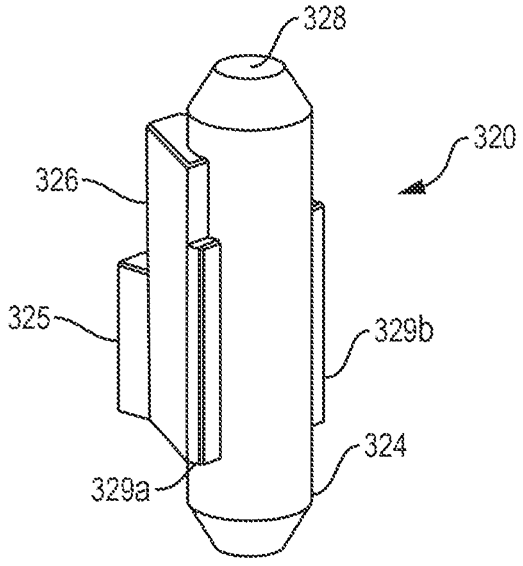
FIG. 6 illustrates an example detector element, alternatively referred to as a detector cell.

The detector cell 320 is further shown in FIG. 6. As illustrated, the detector guide 324 can include an aperture 328 through which an optical cable can be threaded and retained. The detector coupling element 326 includes a projection 325 for engaging with the coupling element 342 of the motorized frame. The detector guide 324 can be retained within the coupling element 326 by retaining elements 329*a*, 329*b*. The detector guide can be releasably retained within the detector cell. The detector guide can also serve as a chassis for accepting a therapeutic or diagnostic device. Two or more detector guides and/or chasses for accepting various tissue detection sensors, therapeutic devices, and diagnostic devices can be included in the device 300.

Figure 7A:
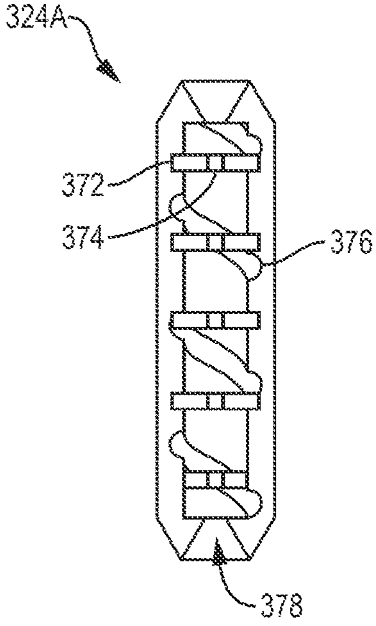
FIG. 7A illustrates an example of internal components of the detector element of FIG. 6 or of a tool delivery element, alternatively referred to as a tool cell.
Figure 7B:
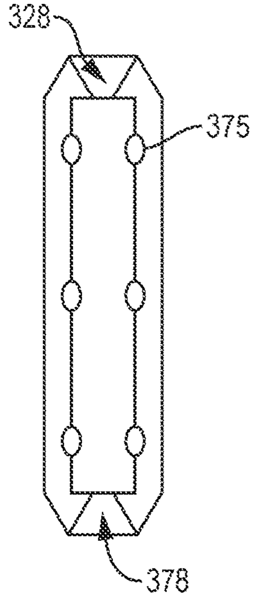
FIG. 7B illustrates another example of internal components of the detector element of FIG. 6 or of a tool delivery element.

Examples of internal configurations of a detector guide are shown in FIGS. 7A and 7B. The detector guide 324A provides for an input port 328 and an output port 378 and includes centering element(s) 372, each of which can define an aperture 374 to orient, for example, an optical cable or a catheter, to a center of the device. The detector guide 324A further includes advancement/retraction elements 376, such as threaded grips. The advancement/retraction elements can enable, for example, an optical cable or a catheter, to advance and/or rotate through the detector cell.

The detector guide 324B includes rollers 375 as advancement elements, which can provide for linear movement and guidance through the detector cell of, for example, an optical cable or catheter. The advancement/retraction elements 375, 376 can comprise, for example a rubber, elastomer, or other flexible, resistant material to engage with the tool being threaded through the detector guide 324.

The detector guide 324 can permit the tissue detection probe or other instrument (e.g., catheter, needle, etc.) to move linearly through the system and/or with a varying amount of rotation, either in a continuous direction (e.g., with a constant or varying velocity) or in changing directions (e.g., proximal and distal directions for advancement and retraction). Based on a combination of rotation and linear movement, the tissue detection probe or other instrument can have a spiral or rifling movement through the cell. A spiral or rifling movement can provide for improved placement of the probe or other instrument in a desired tissue.

The drill bit 312 can be configured to enter bone (e.g., human bone) and can have a diameter of about 200 μm to about 2 mm. The drill bit 312 can have a length configured for drilling to a depth of at least about 7 mm (e.g., about 7 mm to about 15 mm), or at least about 15 mm (e.g., about 15 mm to about 20 mm). The drill bit 312 can have a length configured to drill a depth of any of 5 mm, 6 mm, 7 mm, 8 mm, 9 mm, 10 mm, 11 mm, 12 mm, 13 mm, 14 mm, and 15 mm, for example. The drill bit can be made of titanium, stainless steel, or any other sufficiently strong and stiff material to bore through bone while retaining structural integrity, resisting deflection, and/or providing head dissipation so as to burn tissue during drilling.

The detector cell and/or an optional, additional tool cell can be configured for selective actuation of a therapeutic or diagnostic device after drilling has been completed. Examples of therapeutic and diagnostic devices that can be used with the devices 200, 300 include a cannula (e.g., needle, catheter, trocar, etc.), an electrocautery element, an electrical probe, an intracranial pressure sensor, a biopsy device, and a laser ablation device. Such therapeutic and diagnostic devices can be removably received within the detector cell or an additional tool cell. For example, upon completion of drilling and determination of tissue characteristic(s), the tissue sensor can be removed from the detector cell and the therapeutic or diagnostic device can be inserted. The device 110, 200, 300 can thus provide for insertion and removal of the therapeutic/diagnostic device in the bore generated by the drill bit.

Figure 13:
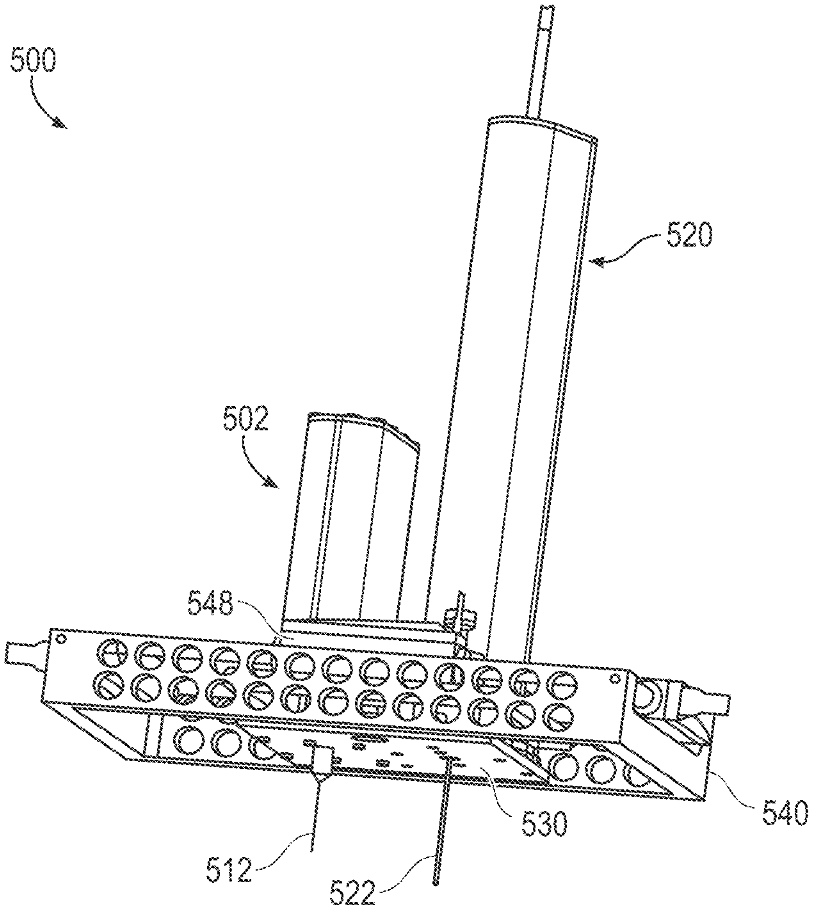
FIG. 13 illustrates another example of a surgical device including a drill and a detector.
Figure 14:
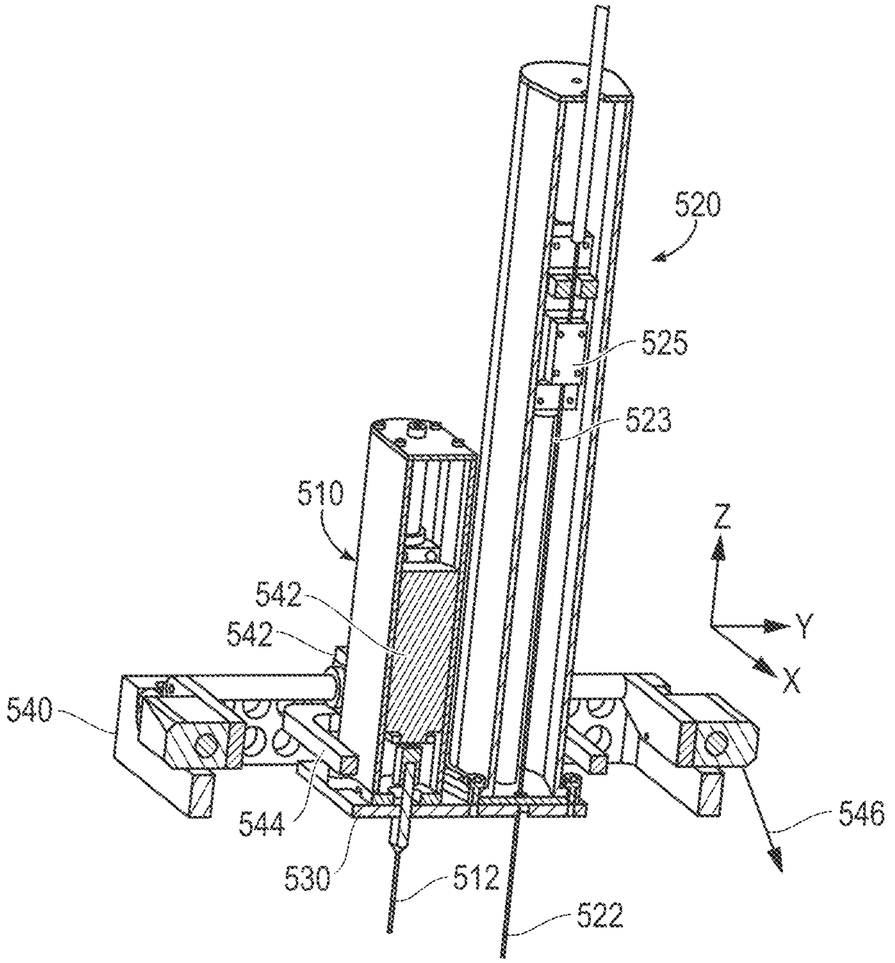
FIG. 14 illustrates internal components of the device of FIG. 12.

Another example configuration of a surgical device 500 is shown in FIGS. 13 and 14. The surgical device 500 includes a drill 510 having a drill bit 512 and a detector 520 having a tissue detection sensor 522. The drill 510 and detector 520 are disposed on a stage element 530 engaged with a motorized frame 540. The motorized frame 540 can include slidable elements 542, 544, and 546, which can be actuable by one or more actuators 548 (e.g., motors, pneumatics) to provide for three degrees of freedom (x, y, z) in placing the drill 510 and detector 520 at a defined location at a subject. The drill and the detector can be independently actuable for insertion and removal of the drill bit 512 and the tissue detection sensor 522 in a bore generated by the drill bit. As illustrated, one or more actuators 516 can be included in the drill cell 510 to actuate linear and rotational movement of the drill bit 512. At least one actuator 525 can be included in the detector cell 520 to actuate linear and rotational movement of a sensor cable 523 (e.g., a fiber optic cable, or, optionally, another tool, such as a catheter).

Figure 15A:
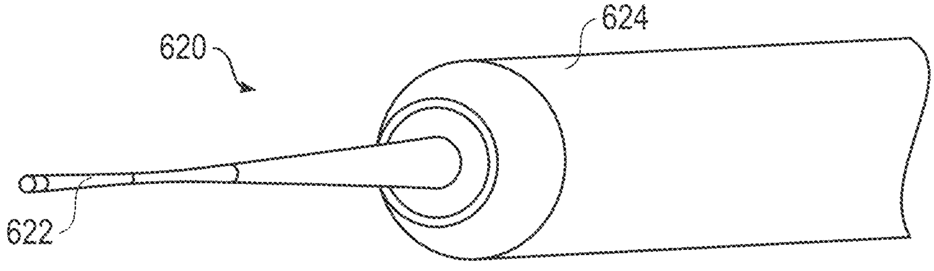
FIG. 15A illustrates an example tissue detection probe.
Figure 15B:
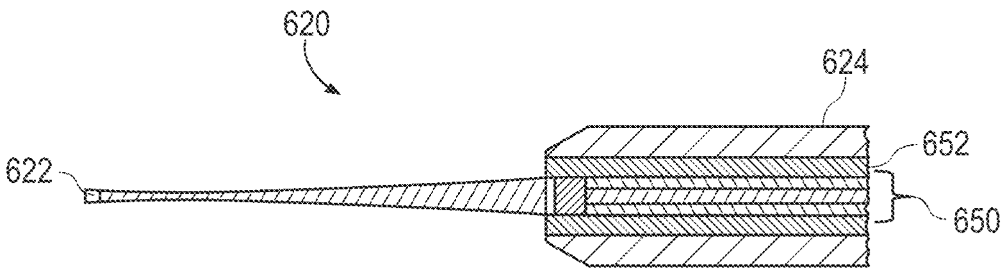
FIG. 15B illustrates internal components of the tissue detection probe of FIG. 15A.

An example of a detector 620 is shown in FIGS. 15A and 15B. The detector 620 can comprise an outer shielding 624, or guide, through which a cable 650 can be disposed. The cable 650 is in operative arrangement with a probe 622. Optionally, additional shielding 652 can be included. The detector 620 can be or include a portion of an OCT device, where the probe 622 comprises an optical aperture and the cable 650 comprises an optical cable. The detector 620 can alternatively comprise other types of sensors. For example, the probe 622 can be an electrical probe for electrical recording and/or electrical stimulation, with cable 650 providing for electrical connection to external components of the detector. In another example, the probe can comprise a tissue sample port and a cable disposed through the detector can comprise a cannula through which a vacuum can be applied to collect a tissue sample.

A diameter of the probe 522, 622 can be less than a diameter of a drill bit 512 such that the probe can be inserted in the bore drilled by the drill bit. Optionally the probe 522, 622 can include a cannula, such as a needle, to provide rigidity or support to at least a part of the exposed portion of the probe.

Where a detector or detector cell comprises an OCT probe, the probe can be a Gradient Index (GRIN) rod. The probe can optionally include one or more galvanometers capable of directing light at a controlled angle into a back aperture of the GRIN rod, thus permitting the angle at which the light exits the GRIN rod to be controlled. An exit angle of the light from the GRIN rod can be scanned in a manner that enables creation of an image on a distal side of the GRIN rod.

The OCT probe can comprise an optical fiber. In an example, the OCT probe can include an optical fiber with a GRIN lens (e.g., imaging needles by Miniprobes (South Australia), optical fiber tips by Agiltron, Inc. (Woburn, MA)). A set of calibration experiments can be performed to determine a transfer function corresponding to the optical fiber or optical fiber-GRIN lens assembly. An OCT probe can optionally comprise a Digital Micromirror Device (DMD), Spatial Light Modulator (SLM), or other light manipulation device that can control the amplitude and/or phase of light entering a back aperture of the optical fiber as a function of spatial position. The DMD and/or SLM can be used to alter an angle of light exiting from the front aperture of the OCT probe, thus permitting the formation of an image.

Optionally, light can emerge from the OCT probe at an angle. This can occur, for example, if the OCT probe is an optical fiber with a GRIN lens at its front aperture, and if the GRIN lens is configured to enable light to exit at a fixed angle relative to an axis of the optical fiber. The OCT probe can be capable of rotating. By translating the OCT probe in the axial direction and rotating the OCT probe, a 3D image can be obtained.

In an example, the detector (e.g., detector 220, 320, 520) comprises a single mode optical fiber including a GRIN lens. In another example, the detector comprises a multimode fiber, and, external of the detector cell and at a proximal end of the fiber, a DMD or SLM is included to vary a focal plane of light being emitted at a distal end of the fiber. A probe of the detector can include at least a distal portion of one or more optical fibers.

As illustrated in FIGS. 13 and 15, the device includes drill and detector cells 510, 520. Optionally, the device can be expanded to include an additional, variable tool cell. Alternatively, or in addition, the detector cell 520 can provide for removal of the cable 523 and can permit insertion and retraction of a therapeutic or diagnostic device with the actuator 525. A diameter of the therapeutic/diagnostic device can be smaller than the diameter of the drill bit 512 so that the device can be inserted into a bore created by the drill bit.

Optionally, the additional tool cell or the therapeutic/diagnostic device can include a sensor encased in a cannula (e.g., a needle) to provide for rigidity. For example, an additional tool can be a pressure sensor disposed within a 26-gauge needle. Additional tool(s) can be any of the following: an electrocautery system, a probe for electrical recording or stimulation, a biopsy punch, a catheter, a tool for extracting CSF, such as a needle and aspirator, a laser ablation system, a chemical sensor, such as an oxygen sensor, and a microdialysis probe.

While the device configurations shown in FIGS. 2-4 and 13-14 are shown as alternative configurations, it should be understood that features or components from each can be combined. For example, a detector cell 320 can comprise an internal configuration similar to that shown with the detector cell 520 (e.g., including an actuator 525 to provide for advancement/retraction). In a further example, the stage element 330 can comprise features similar to those shown with the stage 530 to provide for additional degrees of movement (e.g., slideable elements 542, 544, 546) and/or an actuator 548 to effect movement of the stage.

Figure 18:
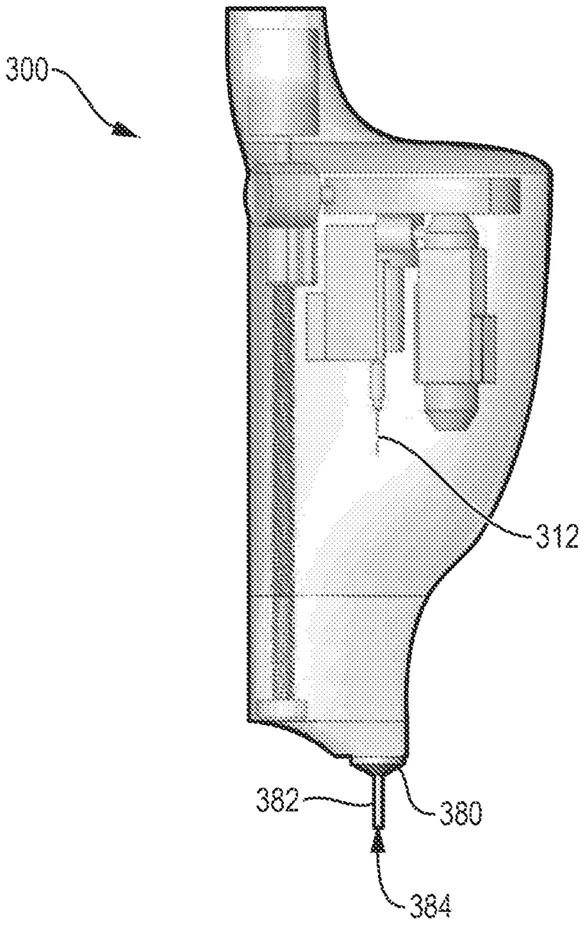
FIG. 18 illustrates an example surgical device including a tissue interface.

A surgical device (e.g., device 300, 500) can further include a tissue interfacing or coupling element, as shown in FIG. 18 and applied to, for example, device 300. The tissue interface 380 can include a rigid cannula 382 and a cutting surface 384. The tissue interface 380 can contact a patient (e.g., a patient's scalp) and can cut through tissues located externally of the bone (e.g., tissues external of the skull). The drill, tissue detection sensor, and, optionally, a therapeutic/diagnostic device, can travel through the cannula portion 382 of the tissue interface 380. The tissue interface can eliminate a need for a scalpel incision and can advantageously provide a consistent and relatively small-sized cut through the external tissue layers of the patient. The tissue interface 380 can also close off an external environment from the surgical site and provide for protection of the drill bit as it travels from the surgical device to the patient. The cannula can be a needle (e.g., a 20-gauge needle) through which the drill can travel. The tissue interface can remain connected to the surgical device 300 throughout a procedure, or the tissue interface can be decouplable from the device 300 but remain attached at the patient, for example, so as to provide an operator with an ability to swap out a tool of the surgical device while retaining the integrity of the surgical site.

A controller (i.e., one or more processors) can be operably coupled to the device 110, 200, 300 and configured to actuate the drill to bore through bone, actuate the drill to retract the drill bit from the bore, actuator the detector to insert the tissue detection sensor into the bore, and determine a tissue characteristic at a distal location of the bore based on a sensed signal from the tissue detection sensor.

The determination of the tissue characteristic can include determination of a change in anatomy or near the distal location, determination of a presence of a blood vessel at or near the distal location, determination of a thickness of a tissue layer at the distal location and/or determination of a density of a tissue layer at the distal location. The determination of the tissue characteristic can inform further drilling, or can inform as to the suitability of the bore location for advancing a therapeutic or diagnostic device.

Tissue detection sensing can be performed by interferometry, including, for example, optical coherence tomography. An interferometry device included as part of a tissue detector can provide for the detection of light, radio, or sound-based waves upon interaction with biological tissue. Where the tissue detector is an OCT probe, blood vessels can be detected by calculation of speckle variance. Speckle variance imaging is generally known in the art and can be used for functional imaging, such as for the detection of blood flow. The detection of blood flow using speckle variance methods can be used to detect the presence of blood vessels or to measure a degree of vascularization in tissue. OCT can also be used for other tissue characterizations, such as a density of tissue, as shown, for example, in the images of FIG. 20.

Other interferometric devices and methods, other than OCT or in conjunction with OCT, can be used for detection of tissue characteristics in the provided surgical devices. For example, the detector (e.g., detector 220, 320, 520) can include an interferometric device that includes a fixed reference, a fixed wavelength laser, and a fixed focal length probe. Translation of the probe can be used to detect tissue boundaries using interferometric methods.

The device can be used to drill into biological tissues where there exists a risk to the tissue if the drill bit encounters a blood vessel. Example control paradigms and methods of operating the device 110, 200, 300, 500 are shown in FIGS. 16 and 17.

Figure 16:
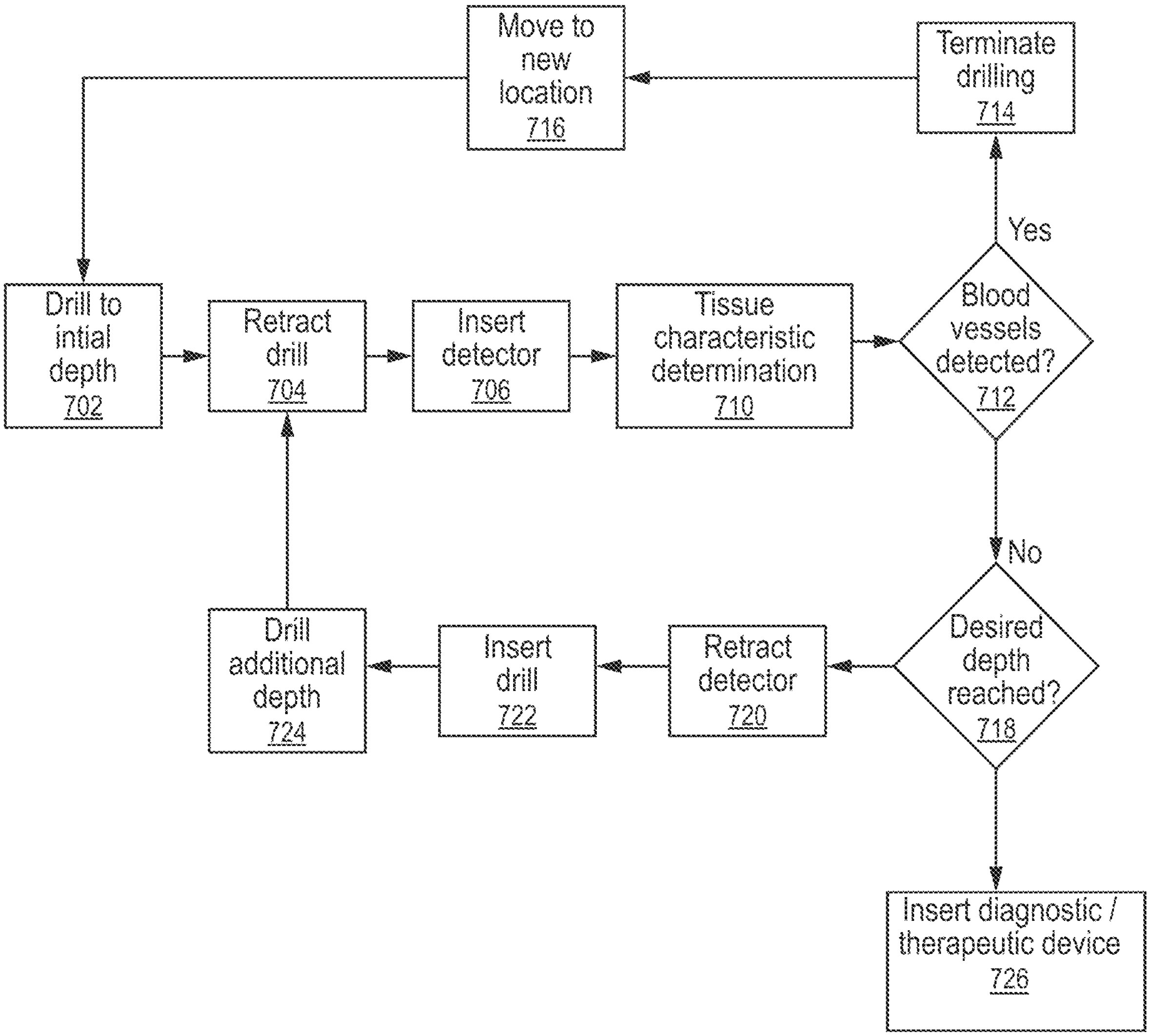
FIG. 16 is a flowchart illustrating example operation of a surgical device.
Figure 17:
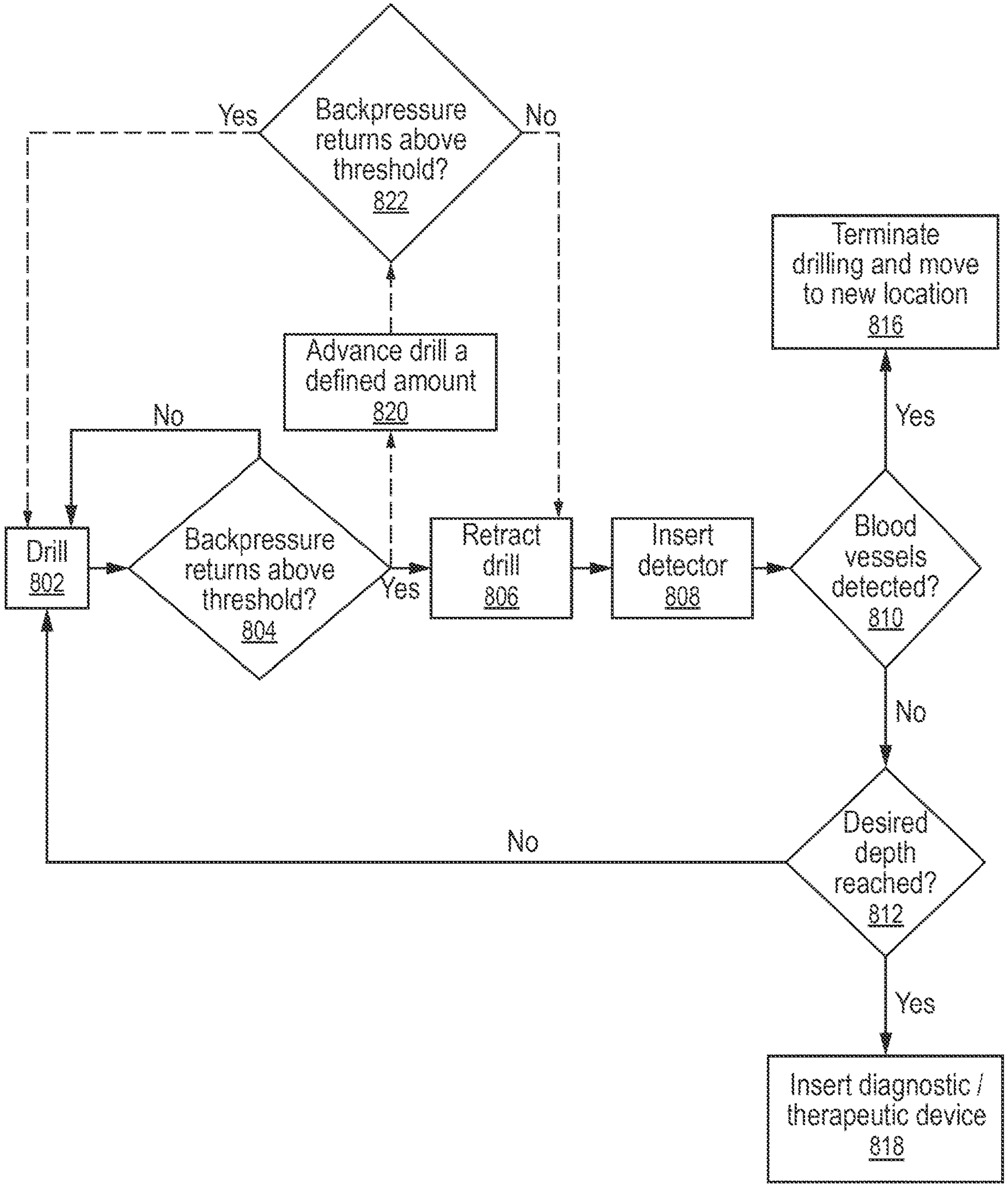
FIG. 17 is a flowchart illustrating example operation of a surgical device having a backpressure sensor.

As shown in FIG. 16, a controller (e.g., controller 260) can be configured actuate the drill bit to descend into the tissue a fixed amount, for example, an amount corresponding to a distance over which there is no risk or minimal risk of encountering a blood vessel (item 702). The drill bit can then be retracted (item 704), and the detector (e.g., OCT probe) can be inserted into the hole or bore produced by the drill (item 706), for example, to a depth slightly less than the depth to which the drill bit was inserted. The OCT probe can then perform a measurement towards determination of a tissue characteristic (item 708), for example, an OCT image for the detection of a presence of blood vessels, and can then be retracted. If blood vessels are detected (item 712), drilling at that location can be terminated (item 714), and the system can move to an alternative location and restart the drilling process (item 716). If blood vessels are not detected, and if the desired drilling depth has not yet been reached (item 718), the detector can be retracted (item 720), the drill bit reinserted (item 722), and drilling can occur for an additional distance (item 724). The additional distance can be chosen such that there is a minimal risk of encountering a blood vessel through the chosen distance, which can be determined based on OCT probe measurements. The process can repeat itself until the OCT probe detects the presence of a blood vessel, or until the drill reaches a desired depth. Once a desired depth is reached, optionally, an additional tool (e.g., a diagnostic or therapeutic device) can be inserted (item 726).

A desired depth may be unknown for some anatomy. The device can instead be operated such that the drill (or a tool) continue traveling until a specific tissue type is reached. A measurement performed by the OCT probe can be used to determine whether the drill has reached the desired tissue type. For example, where the drill is being used to penetrate cranial bone, the OCT may be used both to detect potential blood vessels, and also to determine when the drill has penetrated the cranial bone, based on differences in the optical properties of bone and subcranial tissues.

Alternatively, or in addition, backpressure-sensing automated drilling can occur. In particular, a backpressure sensor and/or a torque sensor in operative arrangement with an actuator of the drill can be used to measure a reactive force (e.g., in range of 0-1 N, 0-3 N, or 0-10 N) exerted upon the drill bit during the drilling process. Backpressure sensing can be used to determine when the drill bit should be stopped. In particular, a sudden drop in backpressure can correspond to a "breakthrough" event, in which the drill bit is moving from a rigid tissue into a less rigid tissue, in which case, there can exist a greater risk of hitting a blood vessel.

As shown in FIG. 17, a controller (e.g., controller 260) can be configured to actuate the drill (item 801) and continuously or periodically monitor readings from a backpressure and/or torque sensor (item 804) to determine when to retract the drill bit (item 806) and insert the detector (e.g., OCT probe) (item 808). In brief, as long as the drill has not achieved the desired depth or encountered the desired tissue type, the controller can continue to monitor readings from the backpressure sensor for signs of a sudden drop in backpressure. When such a drop is detected, the drill can be retracted and the OCT probe can be inserted to a depth that is slightly less than the depth to which the drill had been inserted. The OCT probe can then perform a measurement (item 810). If no blood vessels are detected, and if the desired depth or tissue type has not yet been reached (item 812), then the drill bit can be reinserted and drilling can continue. If blood vessels are detected, the controller can be configured to terminate drilling and move the device to a new location (item 816). If no blood vessels are detected, and if the desired depth or tissue type has been reached, a diagnostic or therapeutic device can be inserted (item 818).

Optionally, upon the detection of a backpressure above a threshold (item 804), the drill can be advanced without rotation through a prespecified distance (item 820), which can be determined based on anatomical properties of the tissue that is being drilled, and backpressure can be further monitored for a return to a value above the threshold (item 822). For example, where the tissue being drilled is cranial bone, the prespecified distance can be chosen to be equal to or less than an average size of voids that are commonly found in cranial bone. If the backpressure on the drill bit does not return to an acceptable level before it is advanced through the prespecified distance, then the drill bit can be retracted and the OCT probe can be inserted to a depth that is slightly less than the depth to which the drill had been inserted. The OCT probe can then perform a measurement. If no blood vessels are detected, and if the desired depth or tissue type has not yet been reached, then the drill bit may be reinserted and drilling may continue.

Figure 8:
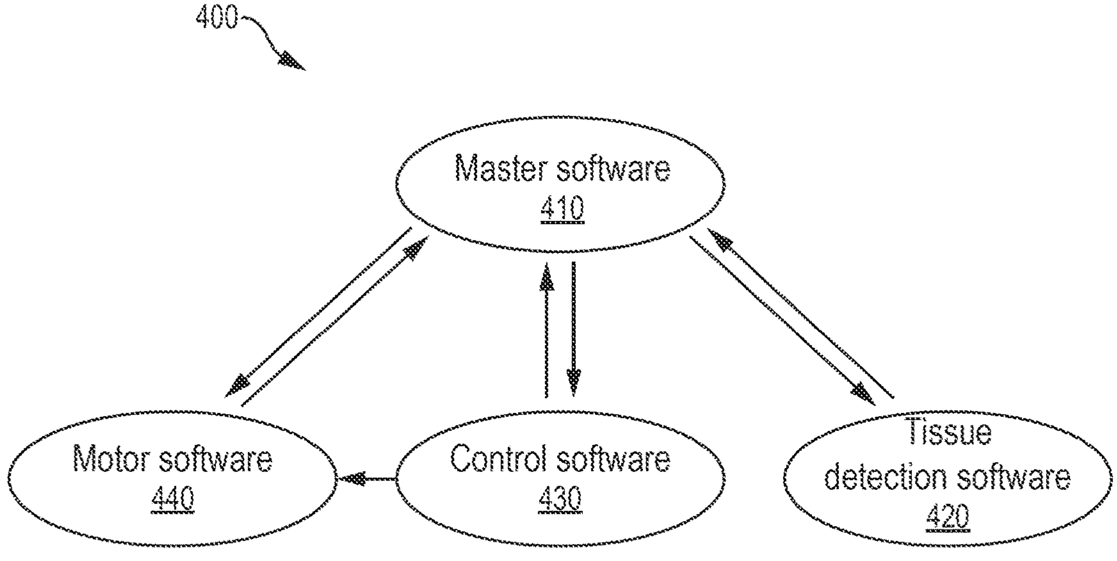
FIG. 8 is a diagram of a software paradigm for a surgical system.

An example software architecture 400 for the system 100 is shown in FIG. 8. As illustrated, a master software 410 interfaces with tissue detection software 420, control software 430, and motor software 440. The master software 410 can determine actions and flow based on information received from user inputs and feedback received from the tissue detection software 420, control software 430, and motor software 440.

Figure 9:
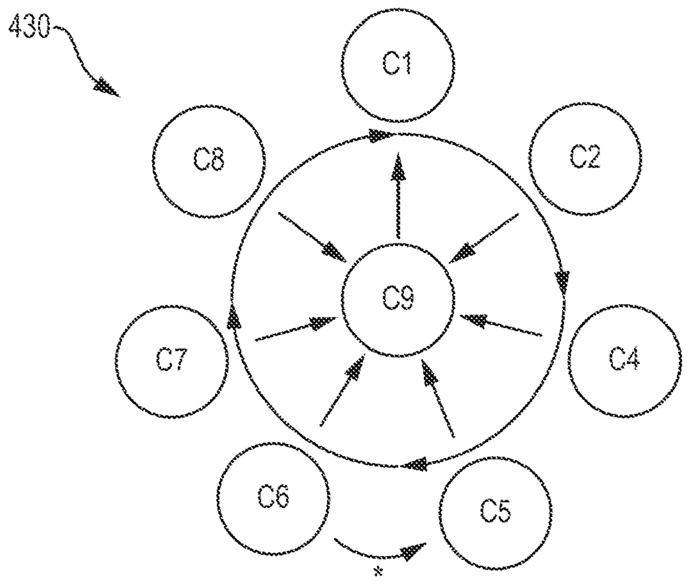
FIG. 9 is a diagram of an example control software architecture for the paradigm shown in FIG. 8.

An example architecture for the control software 430 is shown in FIG. 9. The control software can include various states and feedback loops to control the movement of the drill, and any cell attached to the stage. Based on calculations performed on the output of a compression load cell and torque of the drill motor, the control software can send an appropriate order to the motor software or feedback to the master software. When the bone is determined to be fully drilled, the control software can send a "stop drilling" command and effect removal of the drill cell from the subject. The control software can optionally use other data in addition to compression and torque, such as resistivity, temperature, light refraction, light absorption, or tensile force, to determine breakthrough of the bone.

Example modules C1-C9 of the control software 430 can include any or all of the following, in any combination: (C1) stand by, waiting for any command; (C2) sensor calibration; (C3) reach a surface of the subject to drill; (C4) detect the surface of the subject and commence drilling; (C5) drilling; (C6) verification/check if breakthrough has occurred; (C7) move to OCT mode; (C8) move to needle (or other tool) mode, or reset parameters for a next hole; (C9) emergency stop. An asterisk (*) is provided in the diagram where, if a breakthrough is not confirmed, a return to drilling occurs.

Figure 10:
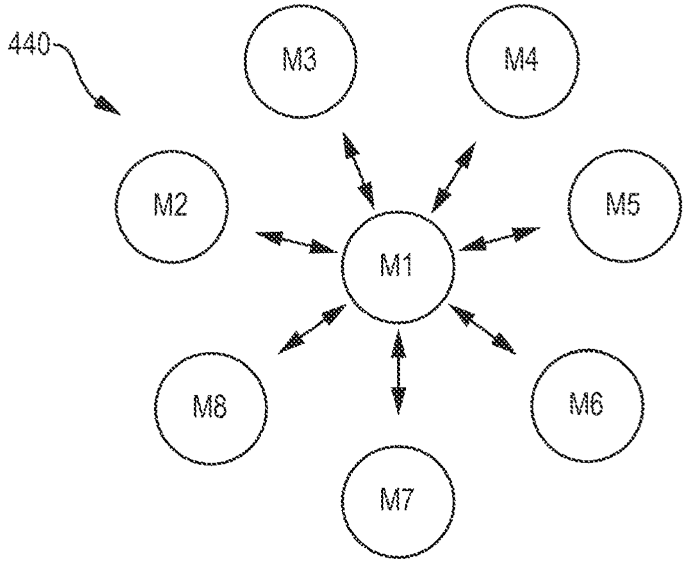
FIG. 10 is a diagram of an example motor software architecture for the paradigm shown in FIG. 8.
Figure 11:
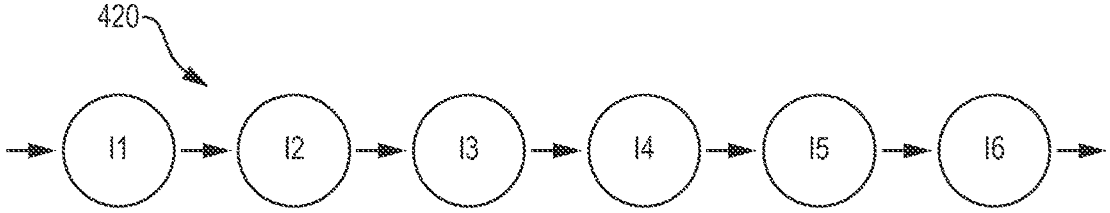
FIG. 11 is a diagram of an example tissue detection software architecture for the paradigm shown in FIG. 8.

An example architecture for the motor software 440 is shown in FIG. 10. The motor software can include various states and loops related to three-dimensional motion of the device, including the positioning of each cell on the stage, movement of each cell to an active location, and linear movement of the cell. Additional cells can optionally be added and moved. The motor software can run orders sent by the master software when the user wants to control the device, or by the control software when operation is automated. The motor software can also be stopped by both the master software and the control software at any time based on the data available.

Example modules M1-M8 of the motor software 440 can include any or all of the following, in any combination: (M1) stand by, waiting for any command; (M2) move the drill down (i.e., in a proximal direction); (M3) move the drill up (i.e., in a distal direction); (M4) return to origin; (M5) stop and wait for a control software command; (M6) move to OCT probe position; (M7) move to needle position; (M8) go to the next registered coordinate.

An example architecture for the tissue detection software 420 is shown in FIG. 10. The tissue detection software can include capturing one or more images with optical coherence tomography, performing image processing and calculations based on the capture image(s), assigning the image(s) a numerical value or range of values, and identifying the tissue material based on the value or range of values, then saving, and providing that data to the master software to be displayed on the controller 108. The captured images can also be shared in real time on the controller 108. The image(s) and calculations can be combined with data obtained from other technologies, including visual (e.g., light refraction), electrical, and thermal technologies.

Example modules I1-I6 of the tissue detection software 420 can include any or all of the following, in any combination: (I1) start scan and harvest raw data; (I2) preprocessing the raw data into phase and intensity data; (I3) processing the data and extracting features; (I4) classification; (I5) saving data; (I6) return feedback.

The automated drilling devices provided can be used to drill holes into materials in which it can be important to avoid contact with fluid channels carrying particles that generate speckle variance signals in the OCT signal. One example of such use is drilling through bone or other tissue where there may be blood vessels located on a distal side of the bone. Punctured blood vessels can create medical complications. The provided devices can optionally be used without cranial imaging, with blood vessel detection providing for determination of a safe entry point. For example, the automated drilling device can be used to drill through cranial bone in cases in which a high-resolution computed tomography or magnetic resonance angiogram of the patient is unavailable and/or in cases in which it is not possible or not desirable to place the patient in a stereotactic frame that would allow for registration of the drilling device to a pre-existing angiogram.

Traditionally, surgeons drill holes in a patient's skull or otherwise remove parts of the skull, relying on their own vision to avoid major blood vessels. When using this technique, it can be necessary for the hole to be large enough that one can see through it. When drilling smaller holes, such as those used for laser interstitial thermal therapy or stereotactic-EEG electrode placement, trajectories are typically carefully planned against preoperative or intraoperative CT or MR imaging. After pre-procedural planning to avoid large blood vessels, the procedure is typically performed blind, without the ability to visualize smaller blood vessels that might be encountered (either because the vessels are poorly visualized on imaging, or due to minor deviation between the preoperative plan and the actual trajectory). By incorporating an OCT probe, or other tissue detection sensor, into a drilling device, particularly in combination with backpressure sensing, blood vessels can be avoided and relatively small holes can be drilled. Such an arrangement carries several advantages, with smaller holes being less prone to infection and more readily healable, and with less resulting trauma for the patient as occurs when a patient has had larger holes drilled.

Once the hole, or bore, has been drilled, additional tools can be inserted into the hole for diagnostic, therapeutic, or other medical purposes.

For example, in the case of trauma patients with a decreased level of consciousness, pressure probes can be inserted into the drilled hole(s) to monitor intracranial pressure. In clinical practice, intracranial pressure monitors are typically inserted during a bedside procedure by a neurosurgeon using a drill several millimeters in diameter, and drilling and sensor insertion are performed blindly. Training is required to perform the procedure safely, due to the blind nature of the procedure, and detecting bleeding or sensor misplacement is difficult for the surgeon to achieve. The provided microsurgical device can allow for direct visualization of the location of probe placement, and can also allow for more accurate placement of probes, including probes small enough that manual placement would be challenging to achieve and, in particular, challenging to accurately place.

As the surgical device and system can be operated in an automated or semi-automated matter, a neurosurgeon or other qualified clinician can monitor use of the device remotely.

In another example, in the case of patients requiring drug delivery to tissues located behind bone (such as the skull), a needle can be inserted with the provided devices, following a drilling and tissue detection procedure, to precisely inject drugs into the intracranial spaces, such as subdural, subarachnoid, parenchymal, or ventricular spaces. Examples of drugs that can be injected this way include viral vectors, antisense oligonucleotides, antibodies, proteins, small molecules, chemotherapeutics, and other agents that do not commonly cross the blood-brain-barrier. To achieve therapeutic effect in the brain, some antibiotics or antifungals require doses that are toxic systemically, and thus cannot reach the full therapeutic concentration desired without an intraventricular drain or surgically implanted reservoir. Furthermore, variable drug concentrations have been noted between lumbar and ventricular CSF (e.g., therapeutic drug concentrations in the lumbar CSF can occur while the drug is undetectable in ventricular space). Further still, many drugs (e.g., some biologics, viruses) that one would like to deliver to the brain are not available in large quantities or are expensive to make, so direct delivery to the brain can reduce the quantity needed by orders of magnitude. For example, viral therapeutics are commonly delivered via craniotomy and intracranial injection for some applications, as are therapeutics in clinical trials for glioma. Furthermore, many drugs have severe side effects when delivered to the whole brain or whole body, so spatially localized delivery can reduce side effects at a given therapeutic dose. Toxic antifungal medications, for example, may only work well in high concentrations near the site of infection. Direct administration near the infection site can reduce toxicity while allowing the drug to reach appropriate therapeutic dosages where needed. A similar problem has been recognized with intrathecal dosing of chemotherapeutics such as methotrexate, where administration via lumbar puncture results in a significantly more variable concentration than direct cranial administration.

In further examples, a needle, catheter, or biopsy punch can be delivered by the provided surgical devices and can be used to extract tissue or CSF for diagnostic purposes. Obtaining a solid or liquid biopsy in such manner provides several advantages. Firstly, dura is emerging as a clinically relevant immune compartment. Particular immune cells associated with disease, as well as cytokines involved in disease response may be present in cerebral CSF and not present in lumbar CSF. In addition, for sampling of cerebrospinal fluid, it has been established that there are aspects of the cerebral CSF that are distinct from the spinal CSF. Some conditions can indicate sampling from the lumbar cisterns, whereas others would indicate sampling from cranial CSF. Moreover, lumbar puncture is widely avoided by patients due to procedural discomfort, postprocedural headache, and other complications, and can require general anesthetic in pediatric patients. Some diseases, such as medulloblastoma, the most common malignant brain tumor in children, may be monitored using CSF sampling, but use of such techniques is limited to the frequency of CSF sampling that can be reasonably performed. Finally, the ability to sample cranial CSF can enable evaluation of drug concentrations in the subarachnoid space, which can be clinically beneficial to ensure therapeutic dosing, but is not currently routinely performed due to difficulty accessing that space. For treatment of certain diseases, such as fungal CNS infections, experts have concluded that CSF drug concentration sampling is critical to improve treatment in this population.

In yet a further example, a probe can be inserted by the provided surgical devices for electrical stimulation or recording, as for patients requiring deep brain stimulation. Non-invasive EEG has a resolution on the order of centimeters and suffers from low signal. On the other hand, epidural and subdural ECoG have resolutions on the order of millimeters or better, and ECOG can achieve signal 20×-100× higher than that of EEG. Furthermore, recording of individual neurons can only be achieved with invasive microelectrodes. However, ECoG and intracranial microelectrodes are rarely applied in practice because surgical placement for such devices is highly invasive. The provided surgical devices can enable electrodes to be inserted to an epidural or subdural level, achieving similar performance to epidural or subdural electrodes, but in a minimally invasive format. These measurement modalities can thus be performed more quickly and for a wider set of indications. Depending on technical specifications, electrical recording can be performed from within the skull (similar to epidural ECoG), beneath the dura (subdural ECoG), or in the brain tissue.

In conjunction with electrical recording, there is wide applicability for minimally invasive stimulation of the brain. In refractory epilepsy, ECoG recordings can be used to detect seizures and trigger stimulation to disrupt seizure activity (responsive neurostimulation). Modalities such as tACS, tDCS, and temporal interference are also being investigated for a wide and growing variety of indications. Examples include enhanced motor recovery after stroke or traumatic brain injury, cognitive modulation for rehabilitation in ALS, and for treatment of neurodevelopmental disorders (e.g. autism spectrum). The provided devices and methods solve several challenges associated with these systems. Systems for responsive neurostimulation are currently implanted via open craniotomy, and can instead be delivered to the brain surface using the provided technology, making such neurostimulation systems more palatable for patients. Non-invasive stimulation paradigms are limited by side effects, such as pain and discomfort caused by stimulation of nerves in the scalp, and it is unclear if the current densities that reach deep brain regions are sufficient for stimulation. Transcranial stimulation systems can achieve higher field strengths with less discomfort. Researchers in this field are optimistic that stimulation using electrodes on the brain surface can result in improved precision and efficacy, increasing the clinical utility of the technology. Furthermore, these paradigms may require long term use, which favor an implantable system.

EXEMPLIFICATION

Example 1. Preclinical Testing Results

Figure 19:
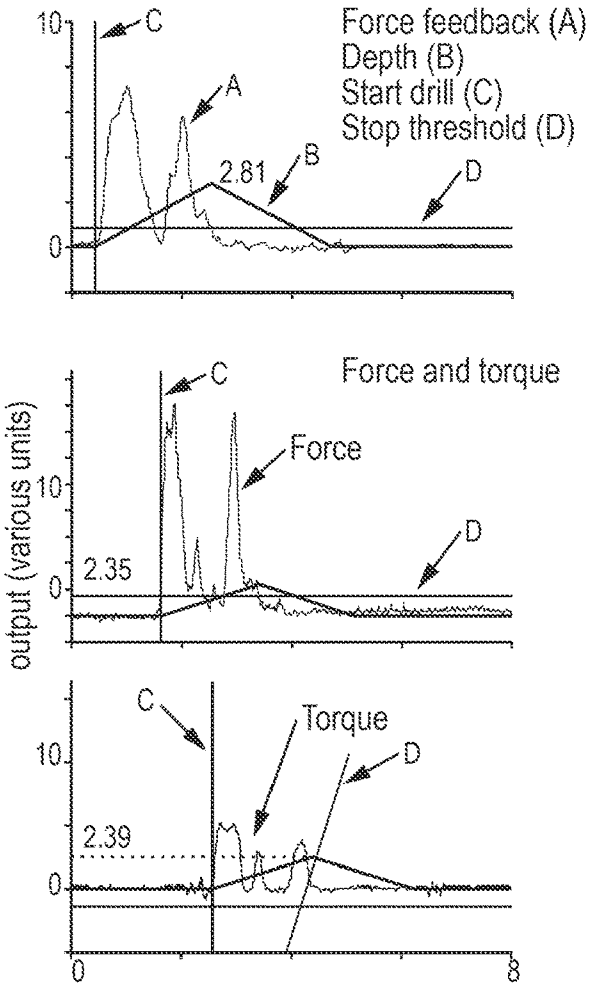
FIG. 19 is a set of graphs illustrating example feedback obtained from device sensors and example thresholding features for operation of the device.

A series of preclinical experiments were conducted on live rabbits to develop and test the hardware, electronics, and software of the surgical system. The method of using a load cell (to measure force applied to the drill bit) and drilling motor torque was created and proven while automatically drilling holes through rabbit skulls. Example data outputs obtained during testing are shown in FIG. 19. Thresholds applied to the force feedback were used to identify the start of skull drilling and used to detect the completion of drilling (and automatic stopping and removal of the drill bit).

Figure 20:
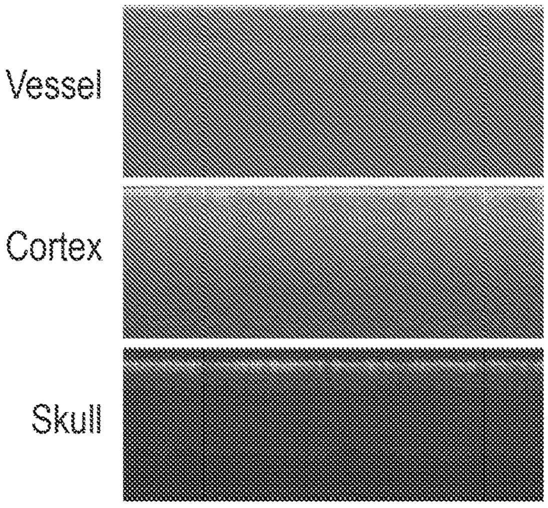
FIG. 20 is a set of images illustrating example tissue detection provided by the device.

Example tissue characteristic detection data is shown in FIG. 20, which includes images captured from the OCT probe of a prototype device. It is clear from this data that the penetration depth of the imaging is dependent on the density of the tissue, enabling a clear differentiation between blood vessels, brain material (cortex), and bone (skull).

What is claimed is:

1. A surgical device for automated drilling, comprising:
a motorized frame;
a drill comprising a drill bit configured to bore through bone;
a detector comprising a tissue detection sensor, the drill and detector independently actuable for insertion and removal of the drill bit and the tissue detection sensor in a bore generated by the drill bit;
wherein the drill and the detector are releasably coupled to a stage element and are configured for selective attachment to the motorized frame; and
the stage element is movable to dispose the selected drill or detector for insertion, removal and respectively drilling or detection of a tissue characteristic upon actuation of the stage element.

2. The surgical device of claim 1, wherein the tissue detection sensor is an optical probe.

3. The surgical device of claim 1, further comprising a backpressure sensor configured to detect a pressure exerted on the drill bit during drilling.

4. The surgical device of claim 1, further comprising a torque sensor configured to detect a torque applied by an actuator of the drill.

5. The surgical device of claim 1, wherein a diameter of the drill bit is less than 1 mm.

6. The surgical device of claim 1, wherein a length of the drill bit is configured for drilling to a depth of at least 7 mm.

7. The surgical device of claim 1, further comprising a tool chassis configured to removably receive a therapeutic or diagnostic device and permit independent actuation of at least a component of the therapeutic or diagnostic device for insertion and removal in the bore generated by the drill bit.

8. The surgical device of claim 7, wherein the therapeutic or diagnostic device is selected from the following: a cannula, an electrocautery element, an electrical probe, a pressure sensor, a biopsy device, and a laser ablation device.

9. The surgical device of claim 7, wherein the tool chassis is configured to removably receive the detector and the therapeutic or diagnostic device.

* * * * *